(12) United States Patent
Mendrok-Edinger et al.

(10) Patent No.: US 11,958,836 B2
(45) Date of Patent: *Apr. 16, 2024

(54) MICRONIZED 1,4-DI(BENZOXAZOL-2'-YL)BENZENE

(71) Applicant: DSM IP ASSETS B.V., Heerlen (NL)

(72) Inventors: Christine Mendrok-Edinger, Kaiseraugst (CH); Alexander Schlifke-Poschalko, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 858 days.

This patent is subject to a terminal disclaimer.

(21) Appl. No.: 16/977,209

(22) PCT Filed: Mar. 19, 2019

(86) PCT No.: PCT/EP2019/056881
§ 371 (c)(1),
(2) Date: Sep. 1, 2020

(87) PCT Pub. No.: WO2019/180042
PCT Pub. Date: Sep. 26, 2019

(65) Prior Publication Data
US 2021/0009570 A1    Jan. 14, 2021

(30) Foreign Application Priority Data

Mar. 20, 2018   (EP) .................... 18162882

(51) Int. Cl.
*C07D 405/12*   (2006.01)
*A61K 9/00*     (2006.01)
*A61K 9/107*    (2006.01)
*A61K 47/22*    (2006.01)

(52) U.S. Cl.
CPC .......... *C07D 405/12* (2013.01); *A61K 9/0014* (2013.01); *A61K 9/107* (2013.01); *A61K 47/22* (2013.01)

(58) Field of Classification Search
CPC .... C07D 405/12; A61K 9/0014; A61K 9/107; A61K 47/22
See application file for complete search history.

(56) References Cited

U.S. PATENT DOCUMENTS 6,030,607 A    2/2000   Linares

FOREIGN PATENT DOCUMENTS

| EP | 1 317 918    | 6/2003 |
| WO | 02/39972     | 5/2002 |
| WO | 2002/039972  | * 5/2002 |

OTHER PUBLICATIONS

International Search Report for PCT/EP2019/056881, dated May 2, 2019, 3 pages.
Written Opinion of the ISA for PCT/EP2019/056881, dated May 2, 2019, 7 pages.
Baeg et al, "Effective UVA and UVB protection from TiO2 UV filter," Aston Chemicals, Personal Care, pp. 51-56, UK, Nov. 2012.
Herzog et al, "Physical properties of organic particulate UV absorbers used in sunscreens," Journal of Colloid and Interface Science 276 (2004) 354-363.

* cited by examiner

*Primary Examiner* — D Margaret M Seaman
(74) *Attorney, Agent, or Firm* — NIXON & VANDERHYE P.C.

(57) ABSTRACT

The present invention relates to a novel micronized 1,4-di (benzoxazol-2'-yl)benzene as well as to the use thereof in topical compositions.

19 Claims, 2 Drawing Sheets

Figure 1: UV-Spectra x-axis: wavelength [nm]; y-axis: E1/1 value

Solid line: DBO–200 dispersion (A) (Invention)

Dotted line: DBO–400 dispersion (A) (Reference)

Figure 2: X-ray powder diffraction measurements

Legend:

x-axis: °2Theta (Cu K-alpha Radiation)
y-axis: Counts/s
lines 1 and 2: XRD of two different batches of crystalline *DBO-200 (C)*
lines 3 and 4: XRD of two different batches of amorphous *DBO-200 (A)*

US 11,958,836 B2

MICRONIZED 1,4-DI(BENZOXAZOL-2'-YL)BENZENE

CROSS-REFERENCE TO RELATED APPLICATIONS

This application is the U.S. national phase of International Application No. PCT/EP2019/056881 filed 19 Mar. 2019, which designated the U.S. and claims priority to EP Patent Application No. 18162882.7 filed 20 Mar. 2018, the entire contents of each of which are hereby incorporated by reference.

FIELD

The present invention relates to a novel micronized 1,4-di(benzoxazol-2'-yl)benzene as well as to the use thereof in topical compositions.

BACKGROUND AND SUMMARY

Sun care products have evolved considerably over the last 40 years. Earlier formulations were intended to protect the user from UV-B radiation (UVB) as was once thought that UV-B rays were the most important contributors to wrinkling, skin disease, and skin cancer. However, more recent studies have shown that UV-A radiation (UVA) is equally or even more important in the development of solar damage and skin diseases, such as lupus erythematosus and melanoma and non-melanoma skin cancers. Thus, today's focus is toward eliminating as much of UVB (290-320 nm) as possible and sufficient UVA (320-400 nm) light in order to avoid skin damages. Nevertheless, modern sun care products should allow skin tanning, which is mainly induced by UVA light. Thus, according to the EU Commission Recommendation of 22 Sep. 2006 on the efficacy of sunscreen products (Official Journal of the European Union L 265/39) today's sun care products should exhibit a sufficient UVA as well as UVB protection, i.e. the ratio of the UVA-protection factor (UVA-PF) to the (UVB) sun protection factor (SPF) should be at least 0.33. This means that the (combination of) UV filter(s) should protect both from UVB and UVA light, with a 3 times higher protection in the UVB than in the UVA range. Moreover, to label the sun care product with the circled acronym UVA on the packaging a critical wavelength value of at least 370 nm must be met.

Accordingly, today's sun care products comprise significant amounts of different UV-filter substances to fulfill the above-mentioned requirements as these requirements are not easy to achieve with one or two UV-filters. This, however, often leads to substantial formulation constraints as most of the commonly used UV-filter substances are either oils or need significant amount of oils to be solubilized. Due to the high oil load such sun care products therefore often exhibit unpleasant sensorial properties which knowingly reduce customer acceptability and thus lead to a reduction of the amounts and/or times the product is applied to the skin, far below the recommended use level.

Thus, there is an ongoing need for novel UV-filters which allow, preferably as stand-alone filter, the formulation of sunscreen products which exhibit at the same time high SPF's and meet the above-mentioned EU UVA protection requirements. Such UV-Filters should furthermore advantageously be water soluble or water dispersible to allow reducing the overall oil load of sun care products.

Lately, with the evolving usage of mobile devices, such as smart phones and tablets, furthermore a new problem arose: the unwanted transfer of oils comprised in sun care products to surfaces, such as touch screens or spectacle glasses, which makes the surface smeary which is, of course, highly unwanted by the end consumer. Accordingly, there is also a need of sun care products, which exhibit a reduced material transfer such as in particular of the oils contained therein to hard surfaces.

PARSOL® MAX (INCI: methylene bis-benzotriazolyl tetramethylbutylphenol, (nano) MBBT) and UVINUL® A2B (INCI: Tris-BiphenylTriazine (nano), TBPT) are two commercially available micronized broadband filters, which were developed to complement the absorption properties of conventional UV-filters by closing the gap between UVA and UVB absorption. However, due to their absorption characteristics, both filters may not be used as stand-alone filters providing at the same time high SPF's while fulfilling the EU recommendation and/or critical wavelength requirements. Thus, these filters must still be combined with conventional UV-filters to achieve the required protection.

WO200239972 discloses insoluble organic particles comprising one or several benzazole and/or benzofurane having a mean particles size selected in the range of 10 nm and 5 μm. Furthermore, WO200239972 discloses an aqueous dispersion of crystalline 1,4-di(benzoxazol-2'-yl)benzene having a mean particle size of 450 nm as well as the use thereof in a crème which provides, even at high use levels, only relatively low SPF's and is thus not suitable for formulating modern, efficient sun care products.

Surprisingly it has now been found that micronizing 1,4-di(benzoxazol-2'-yl)benzene (DBO) to a mean particle size of about 200 nm yields a water dispersible organic UV-filter which fulfills as stand-alone filter all of the above mentioned UV-absorption requirement. Due to its water dispersibility this novel UV-filter is also able to mitigate the current formulation constraints. Furthermore, such a 1,4-di(benzoxazol-2'-yl)benzene also significantly reduces the material transfer of sun care products i.e. the material contained in topical compositions comprising said 1,4-di(benzoxazol-2'-yl)benzene. Thus, this novel UV-filter provides the formulators with more flexibility in the development of modern sun care product.

DETAILED DESCRIPTION

Furthermore, it has surprisingly been found that crystalline 1,4-di(benzoxazol-2'-yl)benzene (DBO) having a mean particle size of about 200 nm next to a relatively low UV-performance also renders formulations more storage instable while the respective solid amorphous form does not only provide excellent UV-protection but also render the formulations more storage stable.

Thus, in a first embodiment, the present invention relates to a micronized 1,4-di(benzoxazol-2'-yl)benzene of formula (I)

having a mean particle size of at most 300 nm.

The term 'mean particle size' as used herein refers to the mean number based particle size distribution $D_n50$ (also known as $D_n0.5$) as determined by laser diffraction e.g. with a Malvern Mastersizer 2000 (ISO 13320:2009).

The term "material transfer" as used herein refers to the mass transfer of the topical composition or some ingredients thereof when the topical composition is applied to a surface and afterwards said surface is brought in contact with a surface of a different object and separated again. By this contact some material is transferred from the first surface to the surface of the different object. The amount of material transferred can be determined by measuring the weight gain of the second object.

In a particular advantageous embodiment, the micronized 1,4-di(benzoxazol-2'-yl)benzene according to the present invention exhibits a $D_n50$ in the range from 50 to 300 nm, more preferably in the range from 100 to 300 nm, most preferably in the range from 120 to 280 nm, such as in the range from 140 to 240 nm or in the range from 150 to 220 nm as determined by laser diffraction (Malvern Mastersizer 2000).

Preferably, in all embodiments of the present invention, the micronized 1,4-di(benzoxazol-2'-yl)benzene according to the present invention furthermore exhibits a $D_n10$ (also known as $D_n0.1$) in the range from 30 to 230 nm, more preferably in the range from 80 to 180 nm, most preferably in the range from 100 to 160 nm as determined by laser diffraction (Malvern Mastersizer 2000).

Preferably, in all embodiments of the present invention, the micronized 1,4-di(benzoxazol-2'-yl)benzene according to the present invention furthermore exhibits a $D_n90$ (also known as $D_n0.9$) in the range from 250 to 350 nm, more preferably in the range from 300 to 400 nm, most preferably in the range from 325 to 375 nm as determined by laser diffraction (Malvern Mastersizer 2000).

Particular advantageous micronized 1,4-di(benzoxazol-2'-yl)benzene according to the present invention exhibit a $D_n10$ in the range from 100 to 160 nm, a $D_n50$ in the range from 150 to 220 nm and a $D_n90$ in the range from 325 to 375 nm as determined by laser diffraction (Malvern Mastersizer 2000).

In an even more preferred embodiment, the micronized 1,4-di(benzoxazol-2'-yl)benzene according to the present invention exhibits an E1/1 value at lambda max (i.e. the wavelength in the absorption spectrum where the absorbance is maximum) of at least 400, preferably of at least 500, most preferably of at least 600. The specific absorbance E1/1 (1cm/1%) is well known to a person skilled in the art and is the extinction corresponding to a concentration of a 1% (w/v) solution or dispersion of the tested compound at an optical thickness of 1 cm.

In all embodiments of the present invention it is furthermore preferred, that the micronized 1,4-di(benzoxazol-2'-yl)benzene is in a solid amorphous form which surprisingly exhibits improved physical properties with regard to UV-absorption/protection, SPF contribution and formulation stability compared to the respective crystalline form.

The term "solid amorphous form," as used herein, refers to solid particles which are formed by fast formation/separation of a solid phase from a liquid phase in a solution or a mixture, so that the solid has no time to selectively form a crystal network and thus the obtained solid is in a predominantly disordered form (also referred to herein as 'solid amorphous 1,4-di(benzoxazol-2'-yl)benzene'), which form can be identified by XRPD analysis as illustrated herein. The solid amorphous 1,4-di(benzoxazol-2'-yl)benzene according to the present invention exhibits improved physical properties with regard to UV-absorption/protection, SPF contribution and formulation stability compared to the respective crystalline form.

The solid amorphous form of micronized 1,4-di(benzoxazol-2'-yl)benzene according to the present invention is characterized by a specific absorbance E 1/1 @ 320 nm of ≥750, preferably of ≥780, while the respective crystalline form exhibits a significantly lower specific absorbance E 1/1, i.e. a E 1/1 @ 320 nm of only 719 (always based on the active). Thus, in a preferred embodiment, the solid amorphous form of 1,4-di(benzoxazol-2'-yl)benzene according to the present invention is characterized by a specific absorbance E 1/1 @ 320 nm of at least 750, more preferably of at least 780. Even more preferably the specific absorbance E 1/1 @ 320 nm is selected in the range from 780 to 850, most preferably in the range from 800 to 845.

The specific absorbance E1/1 (1 cm/1%) is well known to a person skilled in the art and is the (base line corrected) extinction corresponding to a concentration of a 1% (w/v) solution or dispersion of the tested compound at an optical thickness of 1 cm at lambda max (i.e. the wavelength in the absorption spectrum where the absorbance is maximum).

Figure 1:
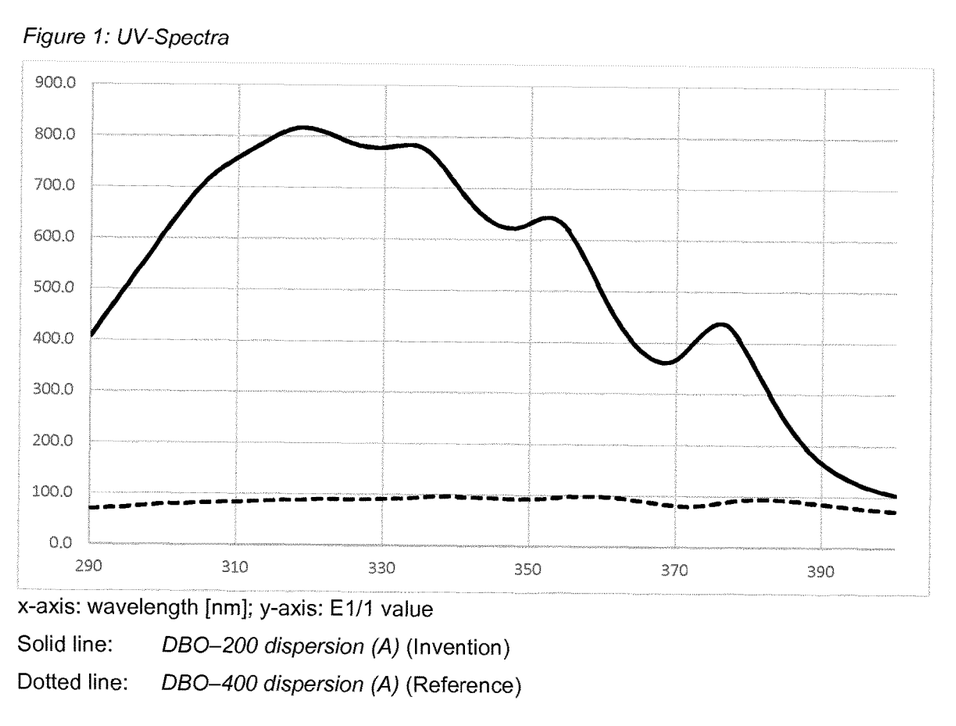
FIG. 1 is a UV-Spectra plot of E1/1 value vs. wavelength (nm) for DPO-200 according to the invention and DBO-400 as a reference as described in the Examples below.
Figure 2:
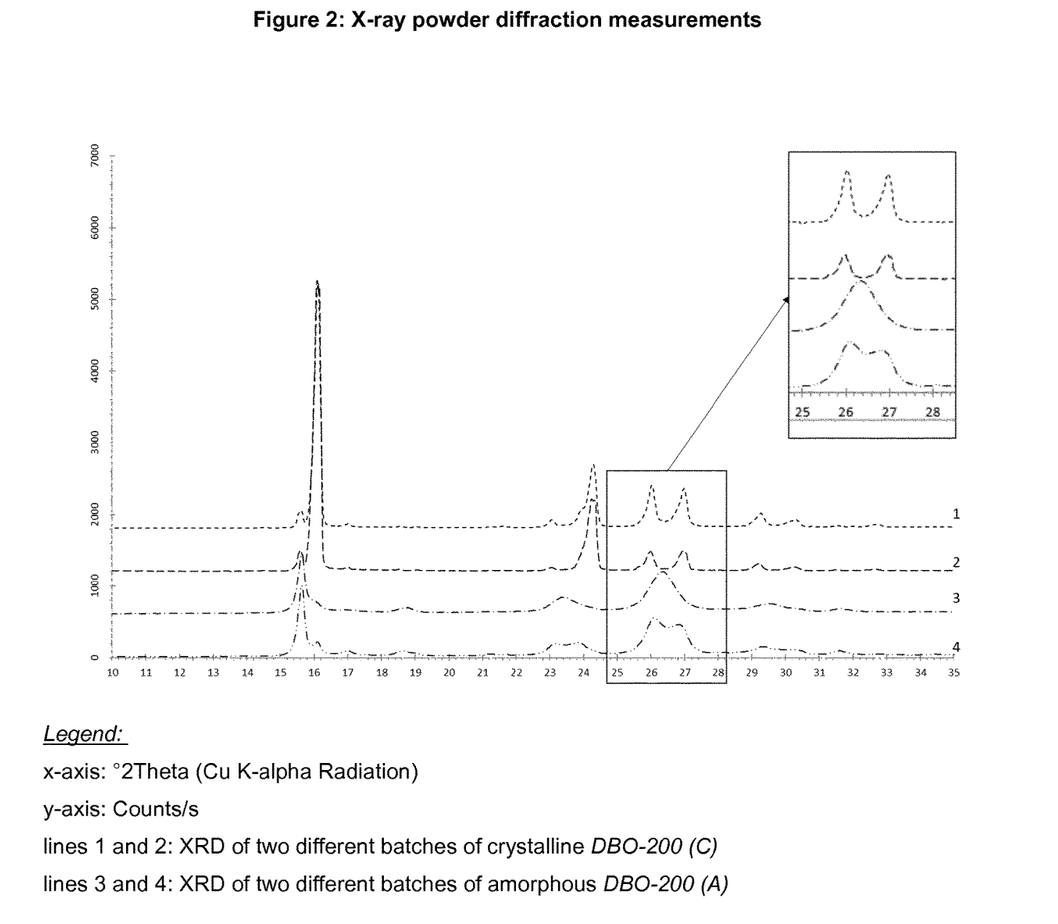
FIG. 2 is a plot of X-ray powder diffraction measurements for different batches of crystalline DBP as described in the Examples below.

The solid amorphous form of the micronized 1,4-di(benzoxazol-2'-yl)benzene is furthermore characterized by an X-ray powder diffraction (XRPD) pattern substantially as depicted in FIG. 2, lines 3 and 4 which is substantially different to the one of crystalline 1,4-di(benzoxazol-2'-yl)benzene (FIG. 2, lines 1 and 2). As can be retrieved from FIG. 1, the crystalline form is characterized by an unambiguous base line separation of the peaks at 25-28 ° 2Theta (Cu K-alpha Radiation), while the solid amorphous form does not exhibit said base line separation. The X-ray diffraction patterns were recorded using a Bruker D8 Advance powder X-ray diffractometer in reflection (Bragg-Brentano) geometry with a LynxEye detector and Cu Kα radiation.

In all embodiments of the present invention the micronized 1,4-di(benzoxazol-2'-yl)benzene according to the present invention preferably exhibits a ratio of UVB to UVA absorbance selected in the range from 0.40 to 0.55, more preferably in the range from 0.44 to 0.54, most preferably in the range from 0.47 to 0.51. The ratio is determined by measuring the UV-spectra of the micronized 1,4-di(benzoxazol-2'-yl)benzene dispersed in water at a concentration of 0.001% (w/v) and calculating the ratio by dividing the area-% from 290 to 320 nm (UVB) through the area-% from 320 to 400 nm (UVA). Said ratio is characteristic for the solid amorphous form of the 1,4-di(benzoxazol-2'-yl)benzene according to the present invention.

In another (or even in an additional) embodiment, the solid amorphous form of 1,4-di(benzoxazol-2'-yl)benzene can also be characterized by its differential scanning calorimetry (DSC) thermogram exhibiting an onset temperature in the range of about 345 to 351 and a heat capacity in the range of about 115-135 J/g. DSC endotherms were recorded using a Mettler Toledo DSC1 (Temperature range: 25° C. to 400° C.; heating rate: 4° C./min) as outlined in the examples.

It is well understood, that the micronized 1,4-di(benzoxazol-2'-yl)benzene according to the present invention is insoluble in common cosmetic oils, wherein the term 'insoluble' refers to a solubility at RT (i.e. ~22° C.) in common cosmetic oils such as e.g. $C_{12-15}$ alkyl benzoate, propyleneglycol, mineral oil but also in water of less than 0.01 wt.-%, preferably of less than 0.05 wt.-%, most preferably of less than 0.03 wt.-% and thus remains in a particular state after incorporation into a topical composition such as a sun care product.

The micronized 1,4-di(benzoxazol-2'-yl)benzene according to the present invention can be produced by standard micronization methods in the art as e.g. outlined in WO9522959 and WO9703643 which are included herein by reference.

The coarse particles of the 1,4-di(benzoxazol-2'-yl)benzene of formula (I), i.e. particles having particle size of >350 nm can for example be prepared by precipitation and/or (re-)crystallization optionally followed by pre-milling (e.g. with a colloidal mill) as e.g. outlined in example 1 of WO2002039972 and illustrated in the examples.

The coarse particles of the solid amorphous form of 1,4-di(benzoxazol-2'-yl)benzene are preferably prepared by a process encompassing the steps of (1) reacting terephthalic acid and 2-aminophenol to form 1,4-di(benzoxazol-2'-yl) benzene and (2) precipitating the thus obtained 1,4-di(benzoxazol-2'-yl)benzene, preferably in the presence of (ice) water to obtain solid amorphous 1,4-di(benzoxazol-2'-yl) benzene. Optionally, the process can contain intermediate purification steps. Alternatively the solid amorphous 1,4-di (benzoxazol-2'-yl)benzene can be further purified by washing with a solvent, in which the 1,4-di(benzoxazol-2'-yl) benzene is only hardly or not soluble such as e.g. toluene and/or an alcohol such as 1-butanol without being limited thereto.

To obtain the micronized 1,4-di(benzoxazol-2'-yl)benzene according to the present invention, the coarse particles are subsequently micronized by conventional grinding methods in the art until a particle size with all the definitions and preferences as given herein is obtained, e.g. by grinding the coarse particles, preferably in the presence of a grinding aid and optionally further customary additives used in the preparation of micronized organic UV-filters, using known grinding apparatus, e.g. a jet, ball, vibration or hammer mill, preferably a high speed stirring mill. Preferably, modern ball mills are used; manufacturers of these types of mill are, for example, Netzsch (LMZ mill), Drais (DCP-Viscoflow or Cosmo), Buhler AG (centrifugal mills) or Bachhofer.

The micronized 1,4-di(benzoxazol-2'-yl)benzene according to the present invention may be used in powder form or as a dispersion thereof. Advantageously, in all embodiments of the present invention, the micronized 1,4-di(benzoxazol-2'-yl)benzene according to the present invention is used in form of an aqueous dispersion thereof e.g. as obtained from wet milling processes.

In a preferred embodiment, the micronized 1,4-di(benzoxazol-2'-yl)benzene according to the present invention is prepared by a wet milling process.

Thus, the present invention also relates to a method of preparing a micronized 1,4-di(benzoxazol-2'-yl)benzene according to the present invention by a wet milling process. In a preferred embodiment the present invention relates to a method of preparing a micronized 1,4-di(benzoxazol-2'-yl) benzene according to the present invention, said method encompassing the step of preparing a mixture of coarse particles of the 1,4-di(benzoxazol-2'-yl)benzene of formula (I), water and optionally grinding aid(s) and/or further additive(s) (in the following referred to as grinding mixture) and grinding said mixture in the presence of milling bodies until the coarse particles of the 1,4-di(benzoxazol-2'-yl) benzene have been converted into the micronized form according to the present invention, i.e. until a particle size with all the definitions and preferences as given herein is obtained. Most preferably, said method encompasses grinding the mixture in a ball mill, most preferably using zirconium silicate balls as milling bodies, until a mean particle size $D_n50$ in the range from 50 to 300 nm, more preferably in the range from 100 to 300 nm, most preferably in the range from 120 to 280 nm, such as in the range from 140 to 240 nm or in the range from 150 to 220 nm is obtained.

The amount of the coarse particles of the 1,4-di(benzoxazol-2'-yl)benzene in said grinding mixture is preferably selected in the range from 10 to 90 wt-%, 20 to 80 wt-% or 30 to 70 wt-%, more preferably in the range from 25 to 60 wt-%, for instance in the range from 25 to 55 wt-%, based on the total weight of the grinding mixture.

The amount of the grinding aid(s) and/or additive(s) (total) in said grinding mixture is preferably selected in the range from 0.01 to 25 wt.-%, more preferably in the range from 2 to 20 wt.-%, most preferably in the range from 3 to 15 wt.-%, such as in the range from 5 to 10 wt.-%, based on the total weight of the grinding mixture.

The term 'additive' as used herein refers to additives commonly used in micronization processes such as in particular in micronization processes to prepare aqueous dispersions of micronized, organic UV-filters. Preferred additives are anti-foam agents, wetting agents, salts, preservatives and thickeners. These additives can either be added before/during grinding or after grinding, e.g. to stabilize the aqueous dispersion of the solid amorphous form of 1,4-di(benzoxazol-2'-yl)benzene according to the present invention obtainable from the wet milling process.

After filtering off the milling bodies, e.g. quartz sand, glass balls or zirconium silicate balls, the filtrate, consisting essentially of the micronized 1,4-di(benzoxazol-2'-yl)benzene according to the present invention, water and optionally the grinding aid(s) and/or additive(s) may be used as such or may be further blended with additives e.g. to stabilize the aqueous dispersion. Alternatively, the filtrate may be dried to obtain the micronized 1,4-di(benzoxazol-2'-yl)benzene in powder form.

In all embodiments of the present invention, the micronized 1,4-di(benzoxazol-2'-yl)benzene is preferably used in the form of the (blended) filtrate, i.e. an aqueous dispersion consisting essentially of the micronized 1,4-di(benzoxazol-2'-yl)benzene according to the present invention, water and optionally the grinding aid(s) and/or additive(s).

Thus, in another embodiment, the present invention also relates to an aqueous dispersion consisting essentially of the micronized UV-filter according to the present invention, water and optionally at least one grinding aid and/or at least one additive.

If the micronized UV-filter according to the present invention is used in the form of an aqueous dispersion thereof, said aqueous dispersion preferably comprises the micronized 1,4-di(benzoxazol-2'-yl)benzene in an amount selected in the range from 10 to 90 wt.-%, 20 to 80 wt.-% or 30 to 70 wt-%, more preferably in the range from 25 to 60 wt.-%, most preferably in the range from 25 to 55 wt.-%, such as in the range from 20 to 40 wt.-% or in the range of 25 to 35 wt.-%, based on the total weight of the aqueous dispersion.

Said aqueous dispersion furthermore comprises preferably at least one grinding aid and/or at least one additive in an amount (total) selected in the range from 0.01 to 25 wt.-%, more preferably in the range from 2 to 20 wt.-%, most preferably in the range from 3 to 15 wt.-%, such as in the range from 5 to 10 wt.-%, based on the total weight of the aqueous dispersion.

Particularly suitable grinding aids according to the present invention are surface-active ingredients, that can be used as dispersing agent such as in particular anionic, non-ionic, amphoteric and cationic surfactants as well as mixture thereof. Such surface-active grinding aids are e.g. disclosed in WO9522959 and WO9703643 which are included herein by reference.

Most preferred in all embodiments according to the invention the at least one grinding aid is an alkyl poly-glucoside.

The term 'alkyl poly-glucoside (APG)' refers to a class of non-ionic surfactants having the generic formula $C_nH_{2+n}O(C_6H_{10}O_5)_xH$, in which n is an integer selected in the range from 2 to 22 and x refers to the mean polymerization level of the glucoside moiety (mono-, di-, tri-, oligo-, and poly-glucosides). These APG's are widely used in household and industrial applications. They are generally derived from renewable raw materials such as glucose derived from corn and plant derived fatty alcohols. These alkyl poly-glucosides generally exhibit a mean polymerisation level of the glucoside moiety ranging from 1 to 1.7, preferably from 1.2 to 1.6 such as from 1.4 to 1.6.

Particularly advantageous alkyl poly-glucosides are $C_{8-10}$ alkyl poly-glucosides consisting essentially of caprylyl ($C_8$) and capryl ($C_{10}$) poly-glucosides. Preferably such caprylyl ($C_8$) and capryl ($C_{10}$) poly-glucosides furthermore exhibit a ratio (%/%, wherein all % are area-% determined by HPLC-MS) of caprylyl ($C_8$) mono-glucoside to capryl ($C_{10}$) mono-glucoside in the range from 3:1 to 1:3, preferably in the range from about 2:1 to 1:2, most preferably in the range from 1.5:1 to 1:1.5. Additionally, such $C_{8-10}$ alkyl poly-glucoside preferably contain no more than 3 wt.-%, more preferably no more than 2 wt.-%, most preferably no more than 1.5 wt.-% of $C_{12}$ alkyl mono-glucoside (as determined by HPLC-MS). It is understood, that such alkyl poly-glucosides are basically free of any higher (i.e. $C1_{4-16}$) alkyl polyglucosides.

A particularly advantageous $C_{8-10}$ alkyl poly-glucoside in all embodiments of the present invention is made from glucose derived from corn and $C_8$ and $C_{10}$ fatty alcohols derived from coconut and palm kernel oils, which is e.g. sold as an aqueous dispersion under the tradename Green APG 0810 by Shanghai Fine Chemical.

Suitable antifoam agents encompass carrier oils, silicone oils and silicone foam inhibitors, hydrophobic silica, hydrophobic fat derivatives and waxes, water-insoluble polymers, amphiphilic components, emulsifiers and coupling agents.

Carrier oils are water-insoluble paraffinic and naphthenic mineral oils, together with vegetable oils such as tall oil, castor oil, soybean oil or peanut oil. Useful agents include residues from the oxo alcohol synthesis, alkylbenzenes, and rude oils from the low-temperature carbonization of brown coal or other bituminous materials.

The most important silicone oils are the polydimethylsiloxanes, in which chain ends are saturated with trimethylsilyl groups. The number of siloxane units represents ranges typically from 2 to 2000.

Silicon antifoam agents are supplied in the form of anhydrous dispersions of pyrogenic or hydrophobized silica in silicone oil. Such mixtures are oily and cloudy. In some cases, they have the consistency of a paste, but the most commonly used foam inhibitors for aqueous systems are 5-50% emulsions.

Further examples of antifoam agents which may be used in the present invention are hydro-phobic silica.

Hydrophobic fat derivatives and waxes include the following materials: fatty acid esters of monofunctional and polyfunctional alcohols; fatty acid amides and sulfonamides; paraffinic hydrocarbon waxes, ozokerite, and montan wax; phosphoric acid mono-, di-, and triesters of short- and long-chain fatty alcohols; short- and long-chain natural or synthetic fatty alcohols; water-insoluble soaps of long-chain fatty acids, including aluminum stearate, calcium stearate, and calcium behenate; perfluorinated fatty alcohols. Examples for water-insoluble polymers are low molecular mass, fatty acid modified alkyl resins; low molecular mass novolaks; copolymers of vinyl acetate and long-chain maleic and fumaric acid diesters; and methyl methacrylate-vinylpyrrolidone polymers. Other relevant polymeric materials include poly (propyleneglycols) and high molecular mass propylene oxide adducts of glycerol, trimethylpropane, pentaerythritol, triethanolamine, dipentaerythritol or polyglycerol, addition products of butylene oxide or long-chain [alpha]-epoxides with polyvalent alcohols.

Amphiphilic compounds include antifoam components with varying water solubility whose foam-inhibiting effects are due to a variety of mechanisms. Examples include sodium oleate and the hardened fish fatty acid soaps used as foam regulators in detergents, nonionic surfactants as modestly ethoxylated alcohols, fatty acids, rosin acids, fatty amines and alkyl- phenol derivatives with HLB (Hydrophilic-Lipophilic Balance) values <10. Further examples are silicon surfactants. These are silicone oils to which polyether groups have been chemically bonded.

Examples for coupling agents are glycols, low molecular mass alcohols or other ingredients known as solubilizer.

If present, the anti-foam agent or mixtures thereof (total amount) is used in amounts from 0.01 to 10 wt.-, preferably from 0.1 to 5 wt.-%, most preferably from 0.5 to 2.5 wt.-%.

Suitable salts include alkali and earth alkaline salts of phosphate, hydroxide such as e.g. disodium hydrogen phosphate and/or sodium hydroxide. If present, the salt or mixtures thereof (total amount) are used in amounts from 0.01 to 5 wt.-, preferably from 0.1 to 4 wt.-%, most preferably from 0.5 to 2.5 wt.-%, based on the total weight of the grinding mixture or the aqueous dispersion.

Suitable thickeners encompass xanthan gum, gellan gum and/or carboxymethylcellulose.

Particularly suitable additives in all embodiments of the present invention are wetting agents such as preferably (poly)propyleneglycol. Most preferably in all embodiments of the present invention the wetting agent is propyleneglycol. Such wetting agent(s) are preferably used in an amount (total) selected in the range from 0.1 to 1 wt.-%, more preferably in an amount of 0.2 to 0.6 wt.-%, based on the total weight of the grinding mixture or the aqueous dispersion.

Particularly suitable anti-foam agents are silicone oils such as in particular polydimethylsiloxanes and/or silicon anti-foam agents such as in particular anhydrous dispersions of pyrogenic or hydrophobized silica in silicone oils. Most preferably in all embodiments of the present invention the anti-foam agent is simethicone. Such anti-foam agent(s) are preferably used in an amount (total) selected in the range from 0 to 1 wt.-%, more preferably in an amount of 0.01 to 0.2 wt.-%, based on the total weight of the grinding mixture or the aqueous dispersion.

Particularly suitable thickeners to be used in the aqueous dispersions encompass xanthan gum, gellan gum and/or carboxymethylcellulose. Most preferably in all embodiments of the present invention the thickener is xanthan gum or gellan gum. Such thickener(s) are preferably used in an amount (total) selected in the range from 0.1 to 1 wt.-%, more preferably in the range from 0.1 to 0.5 wt.-%, based on the total weight of the grinding mixture or the aqueous dispersion.

In a particular advantageous embodiment, the grinding is carried out by dispersing coarse particles of the 1,4-di(benzoxazol-2'-yl)benzene of formula (I) in water in the presence of an alkyl poly-glucoside with all the definitions and preferences as given herein and optionally in the presence of an anti-foam agent such as preferably simethicone, followed by grinding said dispersion with a mill, such as preferably a ball mill, most preferably using zirconium silicate balls, until the coarse particles of the 1,4-di(benzoxazol-2'-yl)benzene of formula (I) have been converted into the micronized form according to the present invention, i.e. until a particle size with all the definitions and preferences as given herein is obtained.

According to a further embodiment, the present invention also relates to topical compositions comprising a micronized 1,4-di(benzoxazol-2'-yl)benzene according to the present invention, respectively preferably an aqueous dispersion thereof, most preferably an aqueous dispersion of a solid amorphous form of 1,4-di(benzoxazol-2'-yl)benzene with all the definitions and preferences as given herein.

The topical compositions of the present invention may be produced by physically blending the micronized 1,4-di(benzoxazol-2'-yl)benzene according to the present invention in powder form or in the form of an aqueous dispersion thereof and a cosmetically acceptable carrier by any conventional method, e.g. by simply stirring the two materials together.

In a preferred embodiment, however, the micronized 1,4-di(benzoxazol-2'-yl)benzene used for the preparation of the topical compositions according to the present invention is used in the form of an aqueous dispersion thereof as e.g. obtainable from a wet-milling process as outlined above.

Advantageously, in all embodiments of the present invention, such aqueous dispersions consist essentially of
(i) 20-70 wt.-%, preferably 25-60 wt.-%, based on the total weight of the aqueous dispersion, of the micronized 1,4-di(benzoxazol-2'-yl)benzene with all the preferences and definitions as given herein,
(ii) 2 to 15 wt.-%, preferably 5 to 10 wt.-%, based on the total weight of the aqueous dispersion, of a $C_{8-16}$ alkyl poly-glucoside with all the preferences and definitions as given above,
(iii) 0 to 3 wt.-%, preferably 0.1 to 2 wt.-%, based on the total weight of the aqueous dispersion of at least one additive, and
(iv) 25 to 60 wt.-%, preferably 30 to 45 wt.-%, based on the total weight of the aqueous dispersion, of water.

The term 'consists essentially of' as used according to the present invention means that the amounts of the ingredients (i) to (iv) sum up to 100 wt.-%. It is, however, not excluded that small amount of impurities or additives may be present which are, for example, introduced via the respective raw materials of the ingredients (i) to (iv).

In a particular advantageous embodiment, the at least one additive is selected from the group consisting of thickeners, wetting agents and anti-foam agents as well as mixtures thereof. Even more preferably at least one thickener and at least on wetting agent is present in the aqueous dispersions according to the present invention. Most preferably, the aqueous dispersions according to the present invention contain as additives (iii-1) propyleneglycol and (iii-2) one thickener selected from xanthan gum or gellan gum and optionally (iii-3) simethicone.

The amount of the micronized 1,4-di(benzoxazol-2'-yl)benzene (based on the active) in the topical composition according to the present invention is preferably selected in the range from 0.1 to 20 wt.-%, more preferably in the range from 0.5 to 15 wt.-%, most preferably in the range from 1 to 10 wt.-%, based on the total weight of the topical composition. Further advantageous ranges are from 2 to 8 wt.-% or from 5 to 7.5 wt.-%.

The topical compositions according to the present invention may be in the form of a suspension or dispersion in solvents or fatty substances, or alternatively in the form of an emulsion or micro emulsion (in particular of oil-in-water (O/W-) or water-in-oil (W/O-)type, silicone-in-water (Si/W-) or water-in-silicone (W/Si-)type, PIT-emulsion, multiple emulsion (e.g. oil-in-water-in oil (O/W/O-) or water-in-oil-in-water (W/O/W-)type), pickering emulsion, hydrogel, alcoholic gel, lipogel, one- or multiphase solution or vesicular dispersion or other usual forms, which can also be applied by pens, as masks or as sprays.

In a particular advantageous embodiment, the present invention also relates to a topical composition according to the present invention which next to the micronized 1,4-di(benzoxazol-2'-yl)benzene comprises at least one oil or fat as such compositions exhibit a significantly reduced material transfer such in particular of the oils or fats contained therein to glass surfaces compared to the respective compositions not containing the micronized 1,4-di(benzoxazol-2'-yl)benzene according to the present invention.

Thus, preferred topical compositions in all embodiments of the present invention are emulsions which contain an oily phase and an aqueous phase such as in particular O/W, W/O, Si/W, W/Si, O/W/O, W/O/W multiple or a pickering emulsions. Most preferred in all embodiments according to the present invention are O/W emulsions, as such emulsions exhibit a significant lower material transfer upon incorporation of a micronized 1,4-di(benzoxazol-2'-yl)benzene according to the present invention compared to a corresponding W/O emulsion.

The amount of the oily phase (i.e. the phase containing all oils and fats including the polar oils) present in such emulsions is preferably at least 10 wt.-%, such as in the range from 10 to 60 wt.-%, preferably in the range from 15 to 50 wt.-%, most preferably in the range from 15 to 40 wt.-%, based on the total weight of the topical composition.

The amount of the aqueous phase present in such emulsions is preferably at least 20 wt.-%, such as in the range from 20 to 90 wt.-%, preferably in the range from 30 to 80 wt.-%, most preferably in the range from 30 to 70 wt.-%, based on the total weight of the topical composition.

In a preferred embodiment, the at least one oil or fat is a liquid UV-filter oil. Thus in another particular embodiment the present invention relates to topical compositions comprising a micronized 1,4-di(benzoxazol-2'-yl)benzene with all the definitions and preferences as given herein and at least one liquid UV-filter oil.

The amount (total) of the liquid UV-filter oil in the topical compositions according to the present invention is preferably selected in the range from 0.1 to 30 wt.-%, more preferably in the range from 1 to 25 wt.-%, most preferably in the range from 5 to 20 wt.-%.

The term 'liquid UV-filter oil' as used herein refers to any substance which absorbs light in the UVB and/or UVA range and which is liquid at ambient temperature (i.e. 25° C.). Such UV-filter oils are well known to a person in the art and encompass in particular cinnamates such as e.g. octyl methoxycinnamate (PARSOL® MCX) and isoamyl methoxycinnamate (Neo Heliopan® E 1000), salicylates such as e.g. homosalate (also known as homomenthyl salicylate, 3,3,5-trimethylcyclohexyl 2-hydroxybenzoate, PARSOL® HMS) and octyl salicylate (also known as ethylhexyl salicylate, 2-ethylhexyl 2-hydroxybenzoate, PARSOL® EHS), acrylates such as e.g. octocrylene (2-ethylhexyl 2-cyano-3,3-d iphenylacrylate, PARSOL® 340) and ethyl 2-cyano-3,3-diphenylacrylate, esters of benzalmalonic acid such as in particular dialkyl benzalmalonates such as e.g. di-(2-ethylhexyl) 4-methoxybenzalmalonate and polysilicone-15 (PARSOL° SLX), dialkylester of naphthalates such as e.g. diethylhexyl 2,6-naphthalate (Corapan® TQ), syringylidene malonates such as e.g. diethylhexyl syringylidene malonate (Oxynex® ST liquid) as well as benzotriazolyl dodecyl p-cresol (Tinoguard® TL).

Particular advantageous liquid UV-filter oils in all embodiments of the present invention are octyl methoxycinnamate, homosalate, octyl salicylate, octocrylene, polysilicone-15, diethylhexyl 2,6-naphthalate, diethylhexyl syringylidene malonate and benzotriazolyl dodecyl p-cresol as well as mixtures thereof.

Most preferably in all embodiments of the present invention the liquid UV-filter oil is selected from the group consisting of octyl methoxycinnamate, homosalate, octyl salicylate, octocrylene, polysilicone-15 as well as mixtures thereof.

The topical compositions according to the present invention are advantageously in the form of an oil-in-water (O/W) emulsion comprising an oily phase dispersed in an aqueous phase in the presence of an O/W emulsifier or in the form of a water-in-oil (W/O) emulsion comprising a water phase dispersed in an oily phase in the presence of a W/O emulsifier. The preparation of such emulsions is well known to a person skilled in the art and illustrated in the examples.

The amount of the oily phase (i.e. the phase containing all oils and fats including the UV-filter oils) present in such O/W or W/O emulsions is preferably at least 10 wt.-%, such as in the range from 10 to 60 wt.-%, preferably in the range from 15 to 50 wt.-%, most preferably in the range from 15 to 40 wt.-%, based on the total weight of the topical composition.

The amount of the aqueous phase present in such O/W or W/O emulsions is preferably at least 20 wt.-%, such as in the range from 20 to 90 wt.-%, preferably in the range from 30 to 80 wt.-%, most preferably in the range from 30 to 70 wt.-%, based on the total weight of the topical composition.

The amount of the at least one O/W emulsifier is preferably selected in the range from 0.5 to 10 wt.-%, more preferably in the range from 0.5 to 5 wt.-%, most preferably in the range from 0.5 to 4 wt.-%, based on the total weight of the topical composition.

The amount of the at least one W/O emulsifier is preferably selected in the range from 0.001 to 10 wt.-%, more preferably in the range from 0.2 to 7 wt.-%, based on the total weight of the topical composition.

Particular advantageous O/W-emulsifiers in all embodiments of the present invention are phosphate ester emulsifier. The most preferred O/W emulsifier according to the invention is potassium cetyl phosphate e.g. commercially available as Amphisol® K at DSM Nutritional Products Ltd Kaiseraugst.

A particular advantageous W/O emulsifiers in all embodiments of the present invention is polyglyceryl-2-dipolyhydroxystearat.

Due to its outstanding absorption properties, further embodiments according to the present invention encompass the use of the micronized 1,4-di(benzoxazol-2'-yl)benzene according to the present invention with all the definitions and preferences as given herein as stand-alone filter, i.e. as sole UV-filter in a topical composition.

Furthermore, the present invention relates to the topical composition according to the embodiments described herein for the use as sunscreen (sun care product), respectively to the use of the topical composition according to the embodiments described herein as sunscreen.

The micronized 1,4-di(benzoxazol-2'-yl)benzene according to the present invention is also suitable to boost the performance of other, conventional UV-filter substances, i.e. is capable of synergistically increase the SPF of a sunscreen composition comprising at least one further UV-filter substance, preferably at least one further UV-B filter substance.

Thus, the present invention also relates to the use of the micronized 1,4-di(benzoxazol-2'-yl)benzene according to the present invention as performance booster, i.e. to synergistically increase the SPF of a sunscreen composition comprising at least one further UV-filter, preferably at least one UVB-filter.

In a further embodiment, the present invention also relates to a method for the use of the micronized 1,4-di(benzoxazol-2'-yl)benzene according to the present invention as described and defined herein in a topical composition comprising at least one oil or fat for reducing the material transfer of the topical composition to surfaces, preferably hard surfaces, most preferably glass or plastic surfaces such as e.g. a touch screen or spectacle glass.

In another embodiment, the invention relates to the use of the micronized 1,4-di(benzoxazol-2'-yl)benzene as described and defined herein to reduce the material transfer, such as in particular of fat(s) and oil(s) contained in a topical composition to a surface such as in particular to a glass or plastic surface such as e.g. a touch screen or spectacle glass.

In a further embodiment, the invention relates to a method to reduce the material transfer such as in particular of fat(s) and/or oil(s) contained in a topical compositions to a surface such as in particular to a glass or plastic surface such as e.g. a touch screen or spectacle glass, said method encompassing the incorporation of a micronized 1,4-di(benzoxazol-2'-yl) benzene as described and defined herein into a topical composition comprising such fat(s) and oil(s).

As the topical compositions according to the invention are intended for topical application, they comprise a physiologically acceptable medium, i.e. a medium compatible with keratinous substances, such as the skin, mucous membranes, and keratinous fibres. In particular the physiologically acceptable medium is a cosmetically acceptable carrier.

The term cosmetically acceptable carrier refers to all carriers and/or excipients and/or diluents conventionally used in cosmetic compositions.

Examples of cosmetic excipients, diluents, adjuvants, additives as well as active ingredients commonly used in the skin care industry which are suitable for use in the topical compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the excipients, diluents, adjuvants, additives etc. can, based on the desired product form and application, easily be determined by the skilled person. The additional ingredients can either be added to the oily phase, the aqueous phase or separately as deemed appropriate.

In an advantageous embodiment, the topical compositions according to the present invention comprise from 50% to 99%, preferably from 60% to 98%, more preferably from 70% to 98%, such as in particular from 80% to 95% of a carrier, based on the total weight of the topical composition.

In a particular advantageous embodiment, the carrier consists furthermore of at least 40 wt. %, more preferably of at least 50 wt.-%, most preferably of at least 55 wt.-% of water, such as in particular of 55 to 90 wt.-% of water.

Particularly suitable oils and/or fats to be comprised in the topical compositions respectively encompassed in the oily phase of the O/W respectively W/O emulsions according to the present invention are liquid UV-filter oils as well as oils commonly used in the preparation of such topical compositions. Preferred liquid UV-filter oils to be used in such topical compositions are octocrylene, octyl methoxycinnamate, homosalate and/or octyl salicylate. Preferred commonly used oils to be used in such topical compositions are glyceryl stearate, stearyl alcohol, isopropyl myristate, caprylic/capric triglyceride as well as mixtures thereof.

The compositions in form of O/W emulsions according to the invention can be provided, for example, in all the formulation forms for O/W emulsions, for example in the form of serum, milk or cream, and they are prepared according to the usual methods. The compositions which are subject-matters of the invention are intended for topical application and can in particular constitute a dermatological or cosmetic composition, for example intended for protecting human skin against the adverse effects of UV radiation (antiwrinkle, anti-ageing, moisturizing, anti-sun protection and the like).

According to an advantageous embodiment of the invention the compositions constitute cosmetic composition which are intended for topical application to the skin.

The term "cosmetic composition" as used in the present application refers to cosmetic compositions as defined under the heading "Kosmetika" in Rompp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), 4th edition, 1992.

Finally, a subject-matter of the invention is a method for the cosmetic treatment of keratinous substances such as in particular the skin, wherein a composition as defined above is applied to the said keratinous substances such as in particular to the skin. The method is in particular suitable to protect the skin against the adverse effects of UV-radiation such as in particular sun-burn and/or photoageing.

The following examples are provided to further illustrate the compositions and effects of the present invention. These examples are illustrative only and are not intended to limit the scope of the invention in any way.

EXAMPLES

1. Preparation of Micronized 1,4-di(benzoxazol-2-yl)benzene 1.1 General Methods

All particles sizes have been determined with a Malvern Mastersizer 2000 (laser diffraction) according to the method as outlined in ISO 13320:2009 and/or a Coulter Delsa Nano S (dynamic laser scattering).

Differential scanning calorimetry (DSC) was performed using Mettler Toledo DSC1 (temperature range from 25° C. to 400° C.; heating rate: 4° C./min; air atmosphere, 2-3 mg samples, average from 2 measurements).

X-ray diffraction patterns were recorded using a Bruker D8 Advance powder X-ray diffractometer in reflection (Bragg-Brentano) geometry. The PXRD diffractometer was equipped with a LynxEye detector. The samples were generally prepared without any special treatment other than the application of slight pressure to get a flat surface. Silicon single crystal sample holder for polymorph screening, 1.0 mm depth. Samples were measured uncovered. The tube voltage was 40 kV and current was 40 mA. A variable divergence slight was used with a 3° window. The step size was 0.02 ° 2θ with a step time of 37 seconds. The samples were rotated at 0.5 rps during the measurement.

E 1/1 values were determined with a UV/(vis) spectrometer (Perkin Elmer Lambda 650S) at 320 nm and a baseline correction according to the following formula: E 1/1=(E 1/1 @ 320 nm)–(E 1/1 @ 650 nm).

The UVB:UVA ratio was determined by measuring the UV-spectra of the respective micronized UV-filter dispersed in water at a concentration of 0.001% (w/v) active and calculating the ratio by dividing the area-% from 290 to 319 nm (UVB) through the area-% from 320 to 400 nm (UVA).

1.2 Preparation of Coarse Particles of Solid Amorphous 1,4-di(benzoxazol-2'-yl)benzene (DBO-400 (A))

A mixture of 702 g polyphosphoric acid and 4.28 ml methanesulfonic acid was heated to 90° C. 65 g terephthalic acid and 107 g 2-aminophenol were added. The mixture was stirred under inert atmosphere at 180° C. for 8 hours and then transferred to ice water. The precipitated product was filtered and washed with water and acetic acid. The precipitate was dispersed in water and the pH adjusted to 8.0 with sodium hydroxide, filtered and washed with water. The crude product was suspended in a mixture of toluene and 1-butanol 3.3:1, stirred at 85° C. for one hour, filtered, washed with diethyl ether, and dried. The resulting coarse particles of solid amorphous 1,4-di(benzoxazol-2'-yl)benzene exhibited a particle size Dn50 of 380 nm (Malvern).

1.3 Preparation of an Aqueous Dispersion of Solid Amorphous 1,4-di(benzoxazol-2'-yl)benzene (DBO-200 Dispersion (A))

A suspension of 175 g of DBO-400 obtained as outlined in (1.2), 324 g of water and 65 g Green APG 0810 was prepared. Afterwards the suspension was milled for 2 h with a LabStar laboratory mill using yttrium-stabilized zirconium oxide grinding beads (0.3mm, from Tosoh Ceramic, Japan) and cooling of the milling chamber (−12° C. brine). After removal of the grinding beads, a 30% aqueous dispersion of micronized 1,4-di(benzoxazol-2'-yl)benzene was obtained.
Particle size:
 Malvern: Dn50 186 nm (Dn10=126 nm, Dn90=355nm)
 Coulter: Mean value (intensity distribution): 171 nm
E 1/1: 839
DSC: onset temperature: 350° C.; heat capacity: 132 J/g.
Ratio UVB:UVA: 0.49
X-ray: FIG. 1, line 4

1.4 Preparation of an Aqueous Dispersion of Crystalline 1,4-di(benzoxazol-2'-yl)benzene (DBO-200 Dispersion (C))

After recrystallisation of coarse particles obtained as outlined in (1.2) from o-dichlorobenzene and drying 73.0% of coarse particles of crystalline 1,4-di(benzoxazol-2'-yl)benzene were obtained, which were subsequently milled in analogy to the process outlined in (1.3). After removal of the grinding beads a 30% aqueous dispersion of crystalline 1,4-di(benzoxazol-2'-yl)benzene was obtained.
Particle size:
Coulter: Mean value (intensity distribution): 193 nm E 1/1: 719;
DSC: onset temperature: 352° C.; heat capacity: 153 J/g.
Ratio UVB:UVA: 0.35
X-ray: FIG. 1, line 2

1.5 Preparation of an Aqueous Dispersion of Coarse Solid Amorphous 1,4-di(benzoxazol-2'-yl)benzene (DBO-400 Dispersion (A))

A suspension of 1.8 g of DBO-400 (A) obtained as outlined in (1.2), 3.51 g of water and 0.69 g of Green APG 0810 was prepared. Afterwards the suspension was mixed at ambient temperature (22° C.) with a magnetic mixture until a homogenous dispersion was obtained. After removal of the magnetic stir bar a 30% aqueous dispersion of micronized 1,4-di(benzoxazol-2'-yl)benzene having a mean particle size Dn50 of 380 nm (Malvern) was obtained.

2. UV Performance in Dependence of Particle Size

The formulations (O/W emulsions) as outlined in table 1 have been prepared according to standard methods in the art.
The in vitro SPF test was performed on PMMA plates (WW5 from Schonberg, 5 cm×5 cm, roughness of 5 µm): 32.5 mg of the respective formulation (i.e. 1.3 mg/cm$^2$) were applied homogenously onto the PMMA plates and dried for 15 minutes.
The in vitro SPF was determined using a Labsphere 2000 UV Transmittance Analyzer: each PMMA plate was measured 9 times at different points on the plate resulting in 27 data points. The result is calculated as the average of these 27 data points.
All measurements were done in triplicates.
The in vitro UVA-PF was determined according to ISO 24443, based on the in vitro SPF.

TABLE 1

Results SPF determination in dependence of the particle size

| INCI | Ref 1 Tinosorb ® S | Ref-2 Uvinul ® A2B | Ref-3 (DBO 400 nm) | Inv-1 (DBO 200 nm) |
|---|---|---|---|---|
| Potassium Cetyl Phosphate | 1.8 | 1.8 | 1.8 | 1.8 |
| Glyceryl Stearate | 2.0 | 2.0 | 2.0 | 2.0 |
| Stearyl alcohol | 2.5 | 2.5 | 2.5 | 2.5 |
| Isopropyl Myristate | 2.0 | 2.0 | 2.0 | 2.0 |
| C12-15 Alkyl Benzoate | 5.0 | 5.0 | 5.0 | 5.0 |
| Caprylic/Capric Triglyceride | 5.0 | 5.0 | 5.0 | 5.0 |
| Xanthan Gum | 0.4 | 0.4 | 0.4 | 0.4 |
| Aqua | q.s. | q.s. | q.s. | q.s. |
| Phenoxyethanol, Ethylhexyl Glycerin | 1.0 | 1.0 | 1.0 | 1.0 |
| Methylene Bis-Benzotriazolyl Tetramethylbutylphenol, Aqua, Decyl Glucoside (50% active) | 7.5* | | | |
| Tris-Biphenyl Triazine, Aqua, Decyl Glucoside (50% active) | | 7.5* | | |
| DBO 400 nm, Aqua, Decyl Glucoside (30% active) DBO-400 dispersion (A) | | | 7.5* | |
| DBO 200 nm, Aqua, Decyl Glucoside (30% active) DBO-200 dispersion (A) | | | | 7.5* |
| In vitro SPF | 13 | 43 | 21 | 56 |
| labeled SPF# | 10 | 30 | 20 | 50 |
| In vitro UVA-PF | 11 | 6 | 16 | 19 |
| Ratio labeled SPF/UVA-PF° | 0.85 | 0.14 | 0.80 | 0.38 |
| Critical wavelength | 385 nm | 372 nm | 382 nm | 378 nm |

*based on active (i.e. 25 wt.-% of the respective dispersion)
on the packaging (according to EU guideline)
°calculated according to the EU guidelines As can be retrieved from the results outlined in table 1, only the micronized UV-filter according to the present invention is able to provide high SPF's while exhibiting at the same time a ratio of SPF/UVA-PF of >0.33 as requested by the EU recommendation.

3. Comparison of UV-Spectra: Solution Vs. Dispersion

The UVB:UVA ratio is determined by measuring the UV-spectra of the respective micronized UV-filter either solubilized in 1-methyl-2-pyrrolidinone or dispersed in water at a concentration of 0.001% (w/v) active and calculating the ratio by dividing the area-% from 290 to 320 nm (UVB) through the area-% from 320 to 400 nm (UVA).

TABLE 2

Comparison of the UV-spectra: solution vs. dispersion

| | Tinosorb ® M | | Uvinul ® A2B | | DBO-200 nm | |
|---|---|---|---|---|---|---|
| | dissolved | dispersed | dissolved | dispersed | dissolved | dispersed |
| Ratio UVB:UVA | 0.63 | 0.37 | 0.91 | 0.64 | 0.31 | 0.49 |

As can be retrieved from table 2 the micronized UV-filter according to the invention surprisingly exhibits a shift into the UVB range upon micronization whereas other micronized organic UV-filters show a shift into the UVA range.

4. UV-Performance Solid Amorphous Versus Crystalline Form

The formulations as outlined in table 3 were prepared according to standard methods in the art. Afterward the in vitro SPF was assessed directly after manufacturing (t0) and after 1-month storage at RT (t1). The invitro SPF test was performed on PMMA plates (WW5 from Schonberg, 5 cm×5 cm, roughness of 5mμ): 32.5 mg of the respective formulation (i.e. 1.3 mg/cm$^2$) were applied homogenously onto the PMMA plates and dried for 15 minutes.

The in vitro SPF was determined using a Labsphere 2000 UV Transmittance Analyzer: each PMMA plate was measured 9 times at different points on the plate resulting in 27 data points. The result is calculated as the average of these 27 data points.

TABLE 3

Results in vitro SPF measurements of solid amorphous vs crystalline form

| Ingredient | Wt.-% | Wt.-% |
| --- | --- | --- |
| Potassium Cetyl Phosphate | 1.8 | 1.8 |
| Glyceryl Stearate | 2.0 | 2.0 |
| Stearyl Alcohol | 2.5 | 2.5 |
| Isopropyl Myristate | 2.0 | 2.0 |
| C12-15 Alkyl Benzoate | 5.0 | 5.0 |
| Caprylic/Capric Triglyceride | 5.0 | 5.0 |
| Xanthan Gum | 0.4 | 0.4 |
| Aqua | Ad 100 | Ad 100 |
| Preservative | 1.0 | 1.0 |
| amorphous DBO (30% active) (DBO-200 dispersion (A)) | 3.0* | |
| crystalline DBO (30% active) (DBO-200 dispersion (C)) | | 3.0* |
| In vitro SPF @ t0 | 9.1 | 6.5 |
| In vitro SPF @ t1 | 8.7 | 2.9 |
| Critical wavelength | 379 | 382 |

*based on the active (i.e. 10 wt.-% of the respective dispersion)

As can be retrieved from table 3 the use of solid amorphous DBO results in a significantly higher SPF compared to the respective crystalline form. Furthermore, such formulations are more storage stable as reflected by an unchanged in vitro SPF after 1-month storage @ RT for the solid amorphous form compared to a significantly reduced SPF after 1-month storage @ RT for of the respective crystalline form.

5. Material Transfer

The material transfer was determined with the sponge test as outlined in the following:
- Cut a sponge cloth (Weitawip Claire, from Weita AG: cellulose/cotton fiber mixture, 200 g/m$^2$, 5 mm thickness) into pieces of 76 mm×26 mm
- Tare the sponge sample
- Apply 400 mg of the respective sample (=cosmetic composition) and distribute homogenously all over the sponge surface of 76 mm×26 mm
- Weigh the sponge with the applied sample
- Tare a microscope slide (glass plate 76 mm×26 mm×1 mm)
- Put the microscope slide (glass plate) on top of the sponge, on which a balance weight of 500 g (height: 6.3 cm, diameter at area of contact: 3.7 cm) is placed for 10 seconds to apply a specific pressure to the sample
- Remove cautiously vertically the microscope slide
- Weigh the removed microscope slide and determine accordingly the amount of sample transferred to the glass plate
- Repeat the test for each composition 10 times to receive an average value (mean value) for each sample.

The formulations as outlined in table 4 have been prepared according to standard methods in the art. Afterward the material transfer was assessed as outlined above.

TABLE 4 material transfer in dependence of the particle size

| INCI | Placebo Wt.-% | Reference Wt.-% | Inv-1 Wt.-% | Inv-2 Wt.-% |
| --- | --- | --- | --- | --- |
| Potassium Cetyl Phosphate | 1.50 | 1.50 | 1.50 | 1.50 |
| Cetyl alcohol | 3.00 | 3.00 | 3.00 | 3.00 |
| Cetearyl alcohol | 1.00 | 1.00 | 1.00 | 1.00 |
| Caprylic/Capric triglyceride | 8.00 | 8.00 | 8.00 | 8.00 |
| Aqua | Ad 100 | Ad 100 | Ad 100 | Ad 100 |
| Glycerin | 3.00 | 3.00 | 3.00 | 3.00 |
| Xanthan Gum | 0.30 | 0.30 | 0.30 | 0.30 |
| Phenoxyethanol, Ethylhexylglycerin | 1.00 | 1.00 | 1.00 | 1.00 |
| Octocrylene | — | 8.00 | — | 8.00 |
| DBO 400 nm, Aqua, Decyl Glucoside (30% active) (DBO-400 nm dispersion (A)) | | 2.4* | | |
| DBO 200 nm, Aqua, Decyl Glucoside (30% active) (DBO-200 nm dispersion (A)) | | | 2.4* | 2.4* |
| Transfer of cream | 2.7% | 1.3% | 1.2% | 0.8% |

*Based on active

As can be retrieved from table 4, the incorporation of the micronized 1,4-di(benzoxazol-2'-yl)benzene according to the present invention into a topical composition comprising at least one oil significantly reduces the amount of the composition transferred to the glass surface rendering the glass surfaces less smeary compared to the references.

The invention claimed is:

1. A micronized solid amorphous 1,4-di(benzoxazol-2'-yl)benzene of formula (I), formula (I)

wherein the micronized 1,4-di(benzoxazol-2'-yl)benzene has a mean particle size Dn50 of 50 nm to 300 nm as determined by laser diffraction, and wherein the 1,4-di(benzoxazol-2'-yl)benzene has a ratio UVB:UVA in a range of 0.40 to 0.55 and a specific absorbance E 1/1 @ 320 nm of ≥780.

2. The micronized solid amorphous 1,4-di(benzoxazol-2'-yl)benzene according to claim 1, wherein the mean particle size is in a range from 120 to 280 nm.

3. The micronized solid amorphous 1,4-di(benzoxazol-2'-yl)benzene according to claim 1, wherein the ratio UVB:UVA of the micronized solid amorphous 1,4-di(benzoxazol-2'-yl)benzene is in a range of 0.44 to 0.54.

4. The micronized solid amorphous 1,4-di(benzoxazol-2'-yl)benzene according to claim 1, wherein the mean particle size is in a range of 150 to 220 nm.

5. The micronized solid amorphous 1,4-di(benzoxazol-2'-yl)benzene according to claim 1, wherein the ratio UVB:UVA of the solid amorphous micronized 1,4-di(benzoxazol-2'-yl)benzene is in a range of 0.47 to 0.51.

6. An aqueous dispersion comprising the micronized solid amorphous 1,4-di(benzoxazol-2'-yl)benzene according to claim 1.

7. The aqueous dispersion according to claim 6, wherein the micronized solid amorphous 1,4-di(benzoxazol-2'-yl)benzene is present in the aqueous dispersion in an amount of 25 to 60 wt.-%, based on the total weight of the aqueous dispersion.

8. The aqueous dispersion according to claim 7, wherein the amount of the micronized solid amorphous 1,4-di(benzoxazol-2'-yl)benzene in the aqueous dispersion is in a range from 25 to 55 wt.-%, based on the total weight of the aqueous dispersion.

9. The aqueous dispersion according to claim 6, wherein the aqueous dispersion further comprises at least one grinding aid and/or at least one additive.

10. The aqueous dispersion according to claim 9, wherein the at least one grinding aid is an alkyl poly-glucoside and the at least one additive is selected from the group consisting of wetting agents, thickeners, anti-foam agents and mixtures thereof.

11. The aqueous dispersion according to claim 9, wherein the at least one additive is selected from the group consisting of propyleneglycol, xanthan gum, gellan gum, simethicone and mixtures thereof.

12. A topical composition comprising the aqueous dispersion according to claim 6.

13. A topical composition comprising the micronized solid amorphous 1,4-di(benzoxazol-2'-yl)benzene thereof according to claim 1.

14. The topical composition according to claim 13, wherein micronized solid amorphous 1,4 di(benzoxazol-2'-yl)benzene is present in the topical composition in an amount in a range from 0.1 to 20 wt. %, based on the total weight of the topical composition.

15. The topical composition according to claim 13, wherein micronized solid amorphous 1,4 di(benzoxazol-2'-yl)benzene is present in the topical composition in an amount in a range from 0.5 to 15 wt. %, based on the total weight of the topical composition.

16. The topical composition according to claim 13, wherein micronized solid amorphous 1,4 di(benzoxazol-2'-yl)benzene is present in the topical composition in an amount in a range from 1 to 10 wt. %, based on the total weight of the topical composition.

17. The topical composition according to claim 13, wherein the topical composition is in the form of an oil-in-water (O/W) emulsion or in the form of a water-in-oil (W/O) emulsion.

18. A method of preparing the micronized solid amorphous 1,4-di(benzoxazol-2'-yl)benzene according to claim 1, wherein the method comprises the steps of
  (a) preparing a mixture of coarse solid amorphous particles of the 1,4-di(benzoxazol-2'-yl)benzene of the formula (I), water and milling bodies and optionally at least one grinding aid and/ or optionally at least one further additive, and
  (b) grinding the mixture of step (a) until the coarse solid amorphous particles of the 1,4-di(benzoxazol-2'-yl)benzene achieve a mean particle size Dn50 of 50 nm to 300 nm.

19. A method of reducing transfer of fat and oil components of a topical composition to a surface, the method comprising the step of incorporating into a topical composition containing the fat and oil components an amount of the solid amorphous micronized 1,4-di(benzoxazol-2'-yl)benzene according to claim 1 which is effective to reduce transfer of the fat and oil components to a surface.

* * * * *